United States Patent [19]

Matteson et al.

[11] Patent Number: 4,701,545

[45] Date of Patent: Oct. 20, 1987

[54] PREPARATION OF α,α-DIHALOALKYL BORONIC ESTERS

[75] Inventor: Donald S. Matteson; Gerald D. Hurst, both of Pullman, Wash.

[73] Assignee: Washington State University Research Foundation, Inc., Pullmann, Wash.

[21] Appl. No.: 828,611

[22] Filed: Feb. 12, 1986

[51] Int. Cl.$^4$ .................. C07C 107/02; C07F 5/04
[52] U.S. Cl. .................................. 558/298; 558/288
[58] Field of Search ............................. 558/298, 288

[56] References Cited

U.S. PATENT DOCUMENTS 4,525,309  6/1985  Matteson et al. ................. 558/298

OTHER PUBLICATIONS

Rathke et al, J. Orgametal. Chem. 122, pp. 145-149 (1976).

Primary Examiner—Helen M. S. Sneed
Attorney, Agent, or Firm—Anthony J. DeLaurentis

[57] ABSTRACT

Esters of α,α-haloalkyl boronic acids are prepared by the addition of an alkali metal dialkylamide, or some other equivalent sterically hindered base to a mixture of a 1,1-dihaloalkane and a trialkyl borate in an organic solvent at a temperature between about $-78°$ C. and $+25°$ C. In one embodiment, diisopropyl (dichloromethyl)borate is formed by the addition of lithium diisopropylamide to a mixture of dichloromethane and triisopropyl borate in the presence of tetrahydrofuran as the solvent medium at a temperature between about $-10°$ C. and $+10°$ C.

26 Claims, No Drawings

PREPARATION OF α,α-DIHALOALKYL BORONIC ESTERS

RELATED APPLICATION

The subject matter of this application is related to that of Ser. No. 475,531, filed Mar. 15, 1983, entitled LEWIS ACID CATALYSIS OF THE HOMOLOGATION OF BORONIC ESTERS WITH HALOALKYLMETAL REAGENTS, now U.S. Pat. No. 4,525,309. The disclosure of U.S. Pat. No. 4,525,309 is incorporated herein by reference.

BACKGROUND OF THE INVENTION

This invention relates to a new and practical process for preparing esters of α,α-haloalkyl boronic acids. More particularly, the invention relates to the preparation of boronic esters having the general structure (I) by the addition of a lithium dialkylamide (II) or other similar sterically-hindered strong base to a mixture of 1,1-dihaloalkane (III) and trialkyl borate (IV), also known as trialkoxyborane, in a suitable solvent such as tetrahydrofuran at a temperature in the range of from about 25° C. to about −78° C. or below. The subject process proceeds in accordance with the following reaction scheme:

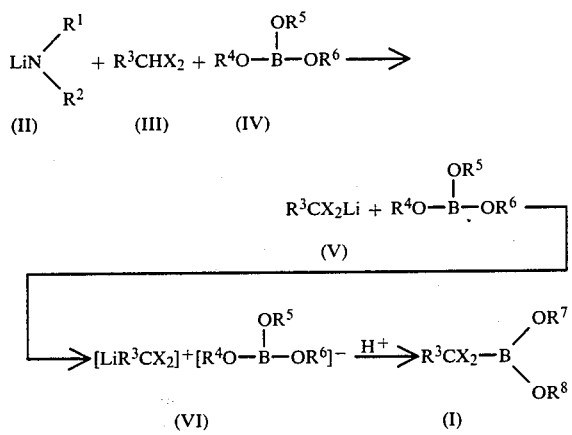

where $R^1$ and $R^2$, independently, are substituted or unsubstitued aliphatic groups, including but not limited to primary, secondary or tertiary alkyl groups, such as methyl, iisopropyl, cyclohexyl and the like, and where $R^1$ and $R^2$ may be the same or different and may be directly linked such that

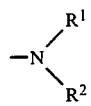

is a cyclic moiety such as 2,2,6,6-tetramethylpiperidide; where $R^3$ is H or a lower primary, secondary or tertiary alkyl group; where $R^4$, $R^5$ and $R^6$, independently, are substituted or unsubstituted aliphatic or aromatic groups, including but not limited to primary, secondary or tertiary alkyl groups, vinylic groups, allylic groups, benzylic groups and the like, and where the function substituents, if present, may comprise any substituents that will allow the formation of (VI), for example alkoxide, ether, ketal, or ester group; where $R^7$ and $R^8$ may be the same or different, and may be the same as $R^4$, $R^5$ and/or $R^6$, or if hydrolysis or transesterification is carried out in the process scheme, may be H or any organic group that can form boronic esters; and where X is a halogen, particularly Br or Cl.

During the course of the reaction scheme, it is theorized that the unstable α,α-dihaloalkyl lithium compound (V) is generated and captured rapidly, before it has time to decompose, by the trialkyl borate (IV) to form an α,α-dihaloalkyl trialkoxyborate salt (VI). Treatment of the salt (VI) with an acid by any of several conventional procedures then yields the product, α,α-dihaloalkyl boronic ester (I).

Dichloromethyl boronic acid and some of its esters were first reported by Rathke et al., *J. Organomet. Chem.* Vol. 122, pp. 145–149 (1976). However, the dichloromethyl lithium required for the synthesis disclosed by Rathke et al cannot be prepared at temperatures much above −100° C. because it decomposes rapidly at higher temperatures. Obviously, the expense of working at such cryogenic temperatures is prohibitive for industrial purposes and higher temperature processes were found to be necessary.

One such process, which is disclosed in Matteson et al, *Organometallics*, Vol. 2, pp 1529–1535 (1983), involves the generation of dichloromethyl lithium in the presence of pinacol butaneboronate at −78° C., whereupon the dichloromethyl lithium is captured efficiently to form an α-chloro boronic ester, i.e., pinacol 1-chloropentylboronate. In U.S. Pat. No. 4,525,309 it was shown that the Matteson et al process could be carried out without the use of pinane butylboronate at 0° C. to produce the analogous pinanediol 1-chloropentylboronate. However, the process disclosed in U.S. Pat. No. 4,525,309 was carried out using a different class of boron compounds having different reactivity, and involves a complex rearrangement process subsequent to the addition of the dichloromethyl group to the boron, which is not similar to the replacement of an alkoxy group by the dihalomethyl group as described in the present invention.

Brown et al, *Organometallics*, Vol. 2, pp 1316–1319 (1983), disclose the preparation of diisopropyl (dichloromethyl) boronate by essentially the same procedure as discussed above in connection with the Rathke et al article, but with an improved product isolation technique. As can be seen from the examples hereinbelow, the products prepared in accordance with the present invention can be isolated by the Brown et al technique, but such isolation is not, in and of itself, part of the present invention.

In another aspect, the present invention provides good yields of dihaloalkyl boronic esters even at temperatures as high as 0° C., which is practical for industrial use, and measurable yields at temperatures as high as 20°–25° C.

The dihaloalkyl boronic esters prepared in accordance with the present invention, such as the achiral diisopropyl (dichloromethyl) boronate, are useful in intermediates for asymmetric synthesis. For example, Sadhu et al., *Organometallics* Vol. 3, pp 804–806 (1984), have shown that chiral 2,3-butanediol (dichloromethyl) boronates, which are easily prepared from the achiral diisopropyl (dichloromethyl) boronate, are useful for preparing chiral α-chloro boronic esters; whereas U.S. Pat. No. 4,525,309 indicates that chiral α-chloro boronic esters are useful intermediates for preparing the insect pheromones brevicomin (western pine beetle)

and (3S-4S)-4-methyl-3-heptanol (European elm bark beetle).

It is to be understood that the one of the primary aspects of the present invention resides in the provision of a practical and efficient route for preparing dihaloalkyl boron compounds at temperatures on the order of 0° C., thereby greatly reducing the inherent cost of producing these useful synthetic intermediates.

DESCRIPTION OF THE INVENTION

The process for preparing dihaloalkyl boronic esters in accordance with the present invention involves the addition of a lithium dialkylamide (II) or other equivalent sterically hindered strong base, such as lithiohexamethyldisilazane or sodium or potassium dialkylamides, to a mixture of a 1,1-dihaloalkane (III) and trialkyl borate (IV) to form an α,α-dihaloalkyl trialkoxyborate salt (VI) which is acidified to form the product α,α-dihaloalkyl boronic ester (I). The α,α-dihaloalkyl trialkoxyborate salt (VI) is believed to be formed when the trialkyl borate (IV) captures an unstable α,α-dihaloalkyl lithium compound (V) which is generated by reaction between the lithium dialkylamide (II) and the 1,1-dihaloalkane (III).

In one aspect, the overall process may be summarized by the following reaction scheme:

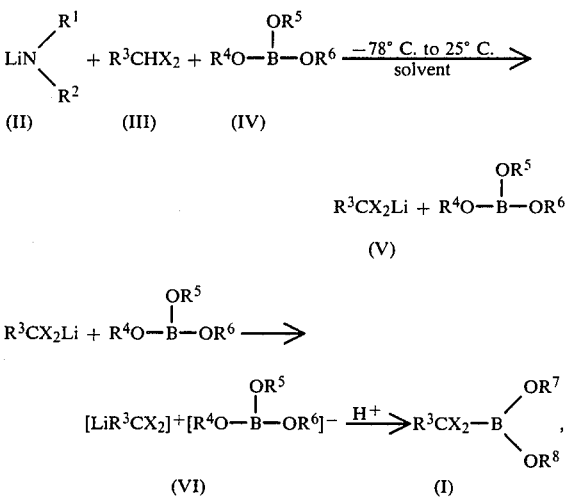

where $R^1$ and $R^2$, independently are substituted or unsubstituted aliphatic groups, including but not limited to primary, secondary or tertiary alkyl groups, and the like, and where $R^1$ and $R^2$ may be the same or different and may be directly linked such that

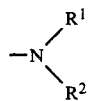

is a cyclic moiety such as 2,2,6,6-tetramethylpiperidide; where $R^3$ is H or a lower primary, secondary or tertiary alkyl group; where $R^4$, $R^5$ and $R^6$, independently, are substituted or unsubstituted aliphatic or aromatic groups, including but not limited to primary, secondary and tertiary alkyl groups, vinylic groups, allylic groups, benzylic groups and the like, and where the functional substituents, if present, may comprise any substituents that will allow the formation of (VI), for example, alkoxide, ether, ketal, or ester group; where $R^7$ and $R^8$ may be the same or different and may be the same as $R^4$, $R^5$ and/or $R^6$, of if hydrolysis or transesterification is carried out in the process scheme, may be H or any organic group that can form boronic esters; and where X is a halogen, particularly Cl or Br.

The conversion of (II) to (V) and then to (VI) may be carried out a temperature between about −78° C. and about 25° C. in a suitable organic solvent medium. Among the solvents that have been found to be useful are included diethyl ether, tetrahydrofuran, petroleum ether, and the like. In a preferred embodiment, tetrahydrofuran would be used as the solvent, and the reaction temperature would be on the order of about −10° C. to about 10° C., although for optimum efficiency the reaction temperature should be about 0° C. or below.

The major features of this invention may be understood more fully by means of the illustrative examples which follow, in addition to the foregoing description. It will be appreciated, of course, that these examples are intended to be typical but not limiting in scope. Unless otherwise indicated, throughout this specification and claims, all temperatures are given in degress Centigrade and all parts and percentages are by weight.

EXAMPLE 1

Preparation of Diisopropyl Dichloromethylboronate [Diisopropoxy(dichloromethyl)borane] [(I), $R^3$=H, $R^7$ and $R^8$=OCH(CH$_3$)$_2$]

A solution of 127 mL (0.55 mol) of triisopropyl borate [(IV), $R^4$=$R^5$=$R^6$=*isopropyl*] *and* 320 ml (5 mol) of dichloromethane in 500 ml of anhydrous tetrahydrofuran was prepared under argon in a 2-l three-neck flask equipped with a mechanical stirrer of the Teflon paddle type and cooled in a bath maintained at −5 to 0° C. In another flask also under argon and at −5° to 0° C. was placed a solution of 84 ml (0.6 mol) of diisopropylamine in 500 mL of tetrahydrofuran to which 320 ml (0.5 mol) of 1.56 molar butyllithium in hexane was added dropwise with stirring in order to form lithium diisopropylamide [(II), $R^1$=$R^2$=isopropyl]. Fifteen minutes after completion of the addition of the butyllithium, the lithium diisopropylamide solution was transferred through a cannular with the aid of argon pressure in order to add it dropwise over the course of about a half hour to the stirred solution of dichloromethane and triisopropyl borate, with both flasks maintained in −5° to 0° C. baths throughout. Throughout this procedure, the solution remained light in color, indicating no significant amount of decomposition of the unstable presumed intermediate, (dichloromethyl)lithium [(V)]. After 15 min more stirring at 0° C., gaseous hydrogen chloride was bubbled into the solution until the methyl orange endpoint was reached, with cooling maintained throughout. Lithium chloride and diisopropylamide hydrochloride precipitated during the course of the acidification and were collected by suction filtration and washed with anhydrous tetrahydrofuran. The filtrate was concentrated with the aid of a rotary evaporator, petroleum ether was added and additional precipitate filtered, and the filtrate was again concentrated. Vacuum distillation yielded a small forerun of triisopropyl borate followed by 55 g (52%) of of diisopropyl dichloromethyboronate [(I), $R^3$=isopropyl], bp 50°–52° C. (5 Torr), which on proton NMR analysis was found to contain approximately 3% triisopropyl borate as the only evident impurity.

EXAMPLE 2

Diisopropyl (Dichloromethyl)boronate at Temperatures Above 0° C.

The procedure of Example 1 was repeated, except that the cooling bath was kept at +3° to +5° C. and the internal temperature of the reaction flask was monitored. The internal temperature rose as high as +9° C. during the addition of (II) to (IV) and the mixture darkened appreciable, indicating some decomposition of the intermediate (V). The yield of diisopropyl (dichloromethyl) boronate (I) was 37%. In another trial, the procedure of Example 1 was repeated with the bath temperature kept at +20° C. In this case the reaction mixture became very dark and the isolated product was mostly unchanged triisopropyl borate. NMR indicated that a small yield of diisopropyl (dichloromethyl)boronate was definitely present as shown by the characteristic proton singlet at δ5.3.

EXAMPLE 3

Diisopropyl (Dichloromethyl)boronate in Ether

The procedure of Example 1 was repeated, except that diethyl ether was used in place of tetrahydrofuran as the solvent, the quantities were scaled down to 0.1 mol of butyllithium with the other reagents proportionally reduced, and the triisopropyl borate was technical grade containing some isopropyl alcohol as an impurity. The yield of diisopropyl (dichloromethyl)boronate (I) was 38%.

EXAMPLE 4

Dimethyl (Dichloromethyl)boronate

The proceudre of Example 1 was followed, except that an equimolar amount of trimethyl borate was used in place of the triisopropyl borates, the quantity of butyllithium was 0.1 mol with the other reagents reduced proportionately, and 2,2,6,6-tetramethylpiperidine was used in place of diisopropylamine. The yield of dimethyl (dichloromethyl)boronate [(I), $R^3=H$, $R^7=R^8=$methyl] was 18%, bp 134°-137° C., confirmed by NMR measurement of the proton singlet at δ5.3, which is characteristic of the dichloromethyl group. In another trial, trimethyl borate was treated with lithium dicyclohexylamide [(II), $R^1=R^2=$cyclohexyl] with the cooling bath maintained at −78° C., and the yield of dimethyl (dichloromethyl)boronate (I) was 17%.

EXAMPLE 5

Diisopropyl (Dibromomethyl)boronate

The procedure of Example 1 was followed, except that the amount of butyllithium was reduced to 0.1 mol with the other reagents in proportion, and an equimolar amount of dibromomethane was used in place of dichloromethane. A small yield of diisopropyl (dibromomethyl)boronate was obtained, confirmed by the singlet in the proton NMR spectrum at δ5.13, characteristic of the dibromomethyl group.

EXAMPLE 6

Dimethyl (1,1-Dichloroethyl)boronate

A modification of the procedure of Example 1 was followed. 1,1-Dichloroethane (25 ml, 0.30 mol) was used in place of dichloromethane and trimethyl borate (30 ml, 0.265 mol) was used in place of triisopropyl borate. The quantity of diisopropylamine was 40 ml and that of butyllithium was 0.25 mol. A −78° C. cooling bath was used. The yield of (I) ($R^3=R^7=R^8=$methyl), bp 48° C. (40 Torr), was 27 g, 55% taking into account the 14% THF indicated by NMR analysis.

Steric hindrance to combination of the base (II) with the boron atom of the boronic ester (IV) is believed to be an important factor in the successful use of this invention. Triisopropyl borate [(IV), $R^4=R^6=R^6=$isopropyl] provides a suitable degree of hindrance to attack by lithium diisopropylamide [(II), $R^1=R^2=$isopropyl], itself a sterically hindered base, so that the (II) attacks dichloromethane faster than it attacks the borate ester (IV), thus generating the essential intermediate, (dichloromethyl)lithium (V, $R^3=H$), which is rapidly captured by the trialkyl borate (IV) to form the stable intermediate (dichloromethyl)trialkoxyborate salt [(VI), $R^3=H$]. In accord with this concept, trimethyl borate (IV, $R^4=R^5=R^6=$methyl) gives lower yields than triisopropyl borate with dichloromethane, but in view of the wide range in steric hindrance spanned by methyl and isopropyl, it may be concluded that any of the easily made and readily available trialkyl borates will work with dichloromethane. With 1,1-dichloroethane, the instability of the intermediate (V) may be a critical factor, and this substrate gave good results with trimethyl borate but not with triisopropyl borate, which would capture the (V) more slowly.

EXAMPLE 7

Diisopropyl (Dichloromethyl)boronate from Lithium Diethylamide

Lithium diethylamide was prepared from 7.5 g (0.103 mol) of diethylamine and 77 mL (0.10 mol) of 1.30 M butyllithium in hexane plus 25 mL of THF to prevent precipitation at 0° C. A solution of 10 mL (0.156 mol) of dichloromethane and 19.3 g (0.105 mol) of triisoproyl borate in 80 mL of THF was cooled to −5° C. with an ice-salt bath, and the cold lithium diethylamide solution was added dropwise to the stirred solution slowly enough that the internal temperature remained at 0° to +5° C. The cooling bath was left in place during distillation of the solvents at pressures down to 0.1 torr into a −78° C. trap. The residue of borate salts was treated with 100 mL of diethyl ether followed by gaseous hydrogen chloride. The brown color of the precipitate obscured the methyl orange endpoint, and excess hydrogen chloride was used. The precipitate (mostly lithium chloride) was filtered and washed with 30 mL more ether, and the combined ether solutions were concentrated. Rapid distillation below room temperature into a −78° C. trap followed by simple redistillation, bp 42°-56° C. (5 torr), 16.1 g. estimated by NMR to contain 91% diisopropyl (dichloromethyl) boronate (14.7 g, 69%), with the remainder entirely triisopropyl borate.

What is claimed is:

1. A process for preparing dihaloalkyl boronic esters, which comprises the step of reacting a sterically hindered strong base with a mixture of dihaloalkane and trialkyl borate in an organic solvent at a reaction temperature between about −78° C. and about +25° C.

2. The process of claim 1, wherein said reaction temperature is between about −10° C. to about +10° C.

3. The process of claim 1, wherein said sterically hindered strong base is a member selected from the group consisting of lithium diisopropylamide, lithium diethylamide, lithium dicylohexylamide, and lithium 2,2,6,6-tetramethylpiperidide.

4. The process of claim 1, wherein said organic solvent is a member selected from the group consisting of tetrahydrofuran, diethyl ether and petroleum ether.

5. The process of claim 1, wherein said trialkyl borate is a member selected from the group consisting of trimethyl borate and triisopropyl borate.

6. The process of claim 1, wherein said dihaloalkane is dichloromethane and the dihaloalkyl boronic ester product is a dialkyl (dichloromethyl)borate.

7. The process of claim 1, wherein said dihaloalkane is dibromomethane and dihaloalkyl boronic ester product is a dialkyl (dibromomethyl) boronate.

8. The process of claim 1, wherein said dihaloalkane is a 1,1-dichloroalkane and the dihaloalkyl boronic ester product is a dialkyl (α,α-dichloroalkyl)boronate.

9. The process of claim 1, wherein said dihaloalkane is 1,1-dichloroethane, wherein said trialkyl borate is trimethyl borate, and the dihaloalkyl boronic ester product is dimethyl (1,1-dichloroethyl)borate.

10. A process for preparing esters of α,α-haloalkyl boronic acids, said esters having the general structure

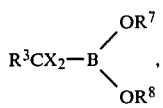

which comprises the steps of:
(1) reacting a sterically hindered base having the structural formula

with a mixture of a dihaloalkane having the formula $R^3CHX_2$ and a trialkyl borate having the structural formula

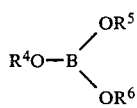

to form a salt having the general formula

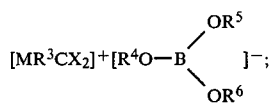

and
(2) converting said salt to the product ester;
said reaction taking place in the presence of an organic solvent and at a reaction temperature in the range of from about −78° C. to about +25° C., and said $R^1$–$R^8$ and X being defined as follows:
M is an alkali metal selected from Li, Na and K;
$R^1$ and $R^2$, independently, are substituted or unsubstituted aliphatic groups and may be directly linked such that

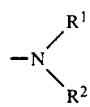

is a cyclic moiety;
$R^3$ is a H or a lower alkyl group;
$R^4$, $R^5$ and $R^6$, independently, are substituted or unsubstituted aliphatic or aromatic groups;
$R^7$ and $R^8$ may be the same or different and may be H or the same as $R^4$, $R^5$ and/or $R^6$; and
X is a halogen.

11. The process of claim 10, wherein said reaction temperature is from about −10° C. to about +10° C.

12. The process of claim 10, wherein

is selected from the group consisting of lithium diisopropylamide, lithium diethylamide, lithium dicyclohexylamide and lithium 2,2,6,6-tetramethylpiperidide.

13. The process of claim 10, wherein said organic solvent is a member selected from the group consisting of diethyl ether, tetrahydrofuran and petroleum ether.

14. The process of claim 10, wherein said trialkyl borate is a member selected from the group consisting of trimethyl borate and triisopropyl borate.

15. The process of claim 10, wherein said dihaloalkane is a member selected from the group consisting of dichloromethane, dibromomethane and 1,1-dichloroethane.

16. The process of claim 10, wherein

is lithium diisopropylamide, and wherein said trialkyl borate is triisopropyl borate.

17. The process of claim 11, wherein

is lithium diisopropylamide, and wherein said trialkyl borate is triisopropyl borate.

18. The process of claim 10, wherein said trialkyl borate is trimethyl borate.

19. The process of claim 10, wherein said dihaloalkane is dichloromethane.

20. The process of claim 10, wherein said dihaloalkane is dibromomethane.

21. The process of claim 10, wherein said dihaloalkane is a 1,1-dihaloalkane.

22. The process of claim 21, wherein said 1,1-dihaloalkane is 1,1-dichloroethane.

23. The process of claim 19, wherein said trialkyl borate is trimethyl borate.

24. The process of claim 21, wherein said trialkyl borate is trimethyl borate.
25. The process of claim 10, wherein said organic solvent is tetrahydrofuran.
26. The process of claim 11, wherein
is lithium diethylamide, and wherein said trialkyl borate is triisopropyl borate.
* * * * *